US008741142B1

(12) United States Patent
Cook

(10) Patent No.: US 8,741,142 B1
(45) Date of Patent: Jun. 3, 2014

(54) FOUR STAGE ANAEROBIC DIGESTER

(75) Inventor: Melvin Wayne Cook, Los Gatos, CA (US)

(73) Assignee: Filtration Dynamics, Inc., Los Gatos, CA (US)

( * ) Notice: Subject to any disclaimer, the term of this patent is extended or adjusted under 35 U.S.C. 154(b) by 507 days.

(21) Appl. No.: 12/969,578

(22) Filed: Dec. 15, 2010

Related U.S. Application Data

(60) Provisional application No. 61/286,773, filed on Dec. 15, 2009.

(51) Int. Cl.
*C02F 3/28* (2006.01)
(52) U.S. Cl.
USPC ............ 210/603; 210/612; 210/632; 210/260
(58) Field of Classification Search
USPC ......... 210/603, 611, 612, 615, 619, 631, 632, 210/252, 259, 260; 435/174
See application file for complete search history.

(56) References Cited

U.S. PATENT DOCUMENTS

| | | | | | |
|---|---|---|---|---|---|
| 3,242,055 | A | * | 3/1966 | De Lucia Santo | 435/176 |
| 4,643,830 | A | * | 2/1987 | Reid | 210/629 |
| 5,637,219 | A | * | 6/1997 | Robinson et al. | 210/603 |
| 5,670,047 | A | * | 9/1997 | Burke | 210/603 |
| 5,753,110 | A | * | 5/1998 | Matsumura et al. | 210/150 |
| 6,299,774 | B1 | * | 10/2001 | Ainsworth et al. | 210/603 |
| 6,673,243 | B2 | * | 1/2004 | Srinivasan et al. | 210/532.2 |
| 6,719,897 | B1 | * | 4/2004 | Maltin | 210/151 |
| 2010/0133176 | A1 | * | 6/2010 | Hansen et al. | 210/603 |

FOREIGN PATENT DOCUMENTS

| | | | |
|---|---|---|---|
| JP | 10-61381 A | * | 3/1998 |
| JP | 2003-39099 A | * | 2/2003 |

* cited by examiner

*Primary Examiner* — Fred Prince

(57) ABSTRACT

A multistage anaerobic digester for treatment of wastewater including complex organic polymers, includes a hydrolysis stage converting the complex organic polymers received at an inlet to solubilized monomers at an outlet; an acidogenesis stage, coupled to the outlet of the hydrolysis stage, converting the solubilized monomers into intermediate products at an outlet of the acidogenesis stage; an acetogenesis stage, coupled to the outlet of the acidogenesis stage, converting the intermediate products into simple molecules at an outlet of the acetogenesis stage; and a methanogenesis stage, coupled to the outlet of the acidogenesis stage, converting the simple molecules to an end product, the end product including a quantity of methane and a quantity of carbon dioxide.

20 Claims, 13 Drawing Sheets

Proposed Auger Housing Configuration – AD #1
(4-Stage Anaerobic Digester)

Proposed Auger Housing Configuration – AD #2
(4-Stage Anaerobic Digester)

Proposed Auger Housing Configuration – AD #3
(4-Stage Anaerobic Digester)

Proposed Auger Housing Configuration – AD #4
(4-Stage Anaerobic Digester)

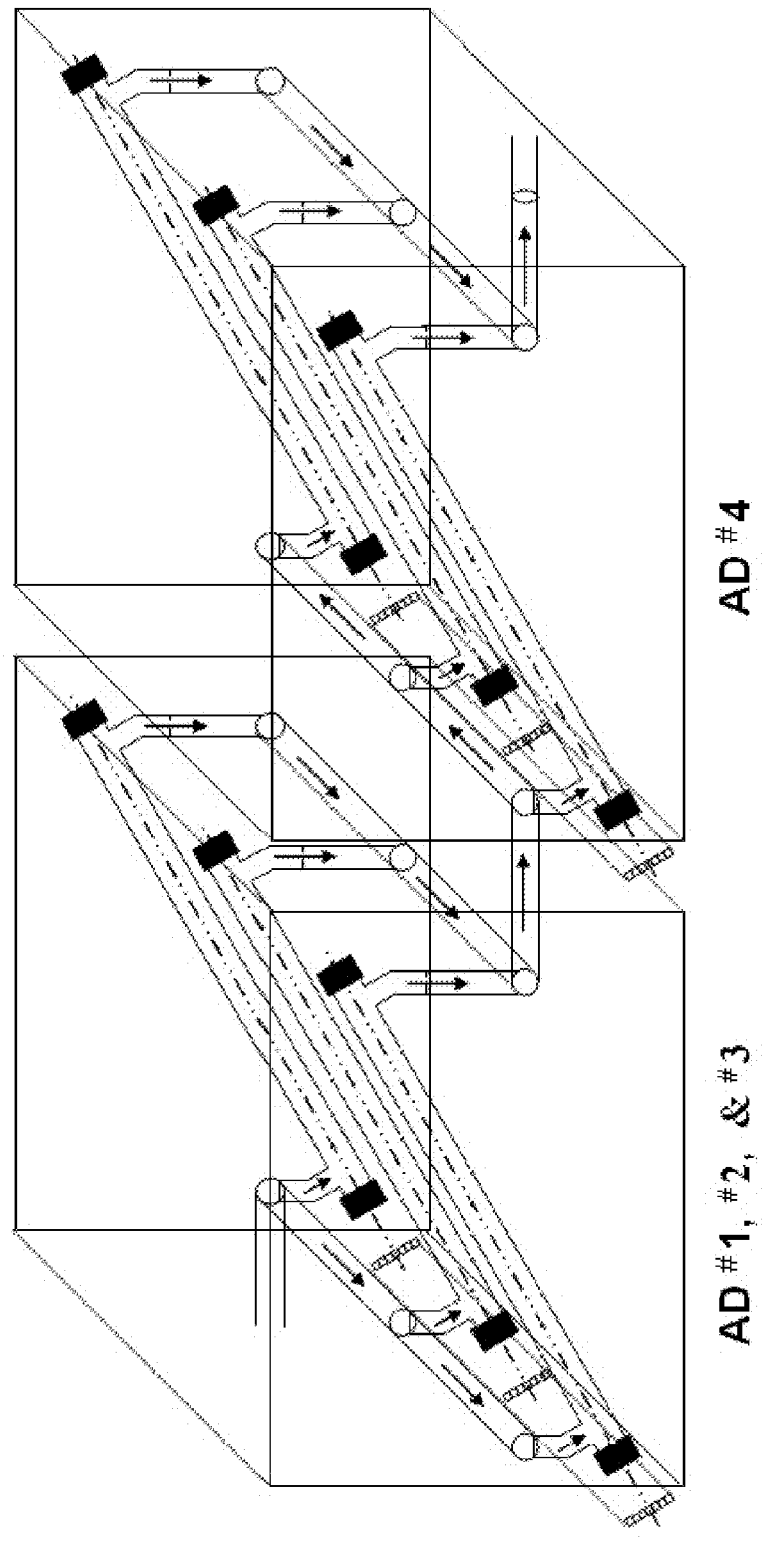

Figure 7  Anaerobic Digester Auger Design

Augers in Parallel – 6" Screw Diameter – 0.5" Pitch
(Influent to Effluent Flow Rate Thru System @ 6.94 gpm = 10,000 gpd)

| Flight Length – Number of Screw Blades: Number of Augers per System: | | 36" – 60 Blades | | | 42" – 70 Blades | | | 48" – 80 Blades | | |
|---|---|---|---|---|---|---|---|---|---|---|
| | | 12 | 18 | 24 | 12 | 18 | 24 | 12 | 18 | 24 |
| Total Pitch Volume of System | gal | 87 | 131 | 175 | 102 | 153 | 204 | 117 | 175 | 233 |
| Screw Surface Area of System (Both Sides of Screw) | ft² | 281 | 420 | 561 | 327 | 491 | 654 | 374 | 561 | 748 |
| Pitch Volume of Auger | gal | 7.3 | 7.3 | 7.3 | 8.5 | 8.5 | 8.5 | 9.7 | 9.7 | 9.7 |
| Screw Surface Area of Auger (Both Sides of Screw) | ft² | 23.4 | 23.4 | 23.4 | 27.3 | 27.3 | 27.3 | 31.2 | 31.2 | 31.2 |
| Screw Length Across Auger (Influent to Effluent) | ft | 43.2 | 43.2 | 43.2 | 50.4 | 50.4 | 50.4 | 57.6 | 57.6 | 57.6 |
| Substrate Flow Rate (Thru Each Auger) | ft/min | 3.4 | 2.3 | 1.7 | 3.4 | 2.3 | 1.7 | 3.4 | 2.3 | 1.7 |
| Substrate Retention Time (Within Each Auger) | min | 12.6 | 18.9 | 25.2 | 14.7 | 22.0 | 29.4 | 16.8 | 25.5 | 33.6 |
| RPM To Move Substrate (Thru Each Auger) | min | 4.77 | 3.18 | 2.38 | 4.77 | 3.18 | 2.38 | 4.77 | 3.18 | 2.38 |

| Letter | Description |
|---|---|
| A | Screw Diameter |
| B | Root Diameter |
| C | Pitch |
| D | Overall Length of Flight |
| E | Flight Thickness |
| F | Shaft Length |

| Letter | Description |
|---|---|
| G | Shaft Diameter |
| H | Keyway (if required) |
| I | Shaft Length |
| J | Shaft Diameter |
| K | Keyway (if required) |
| L | Overall Length of Auger |

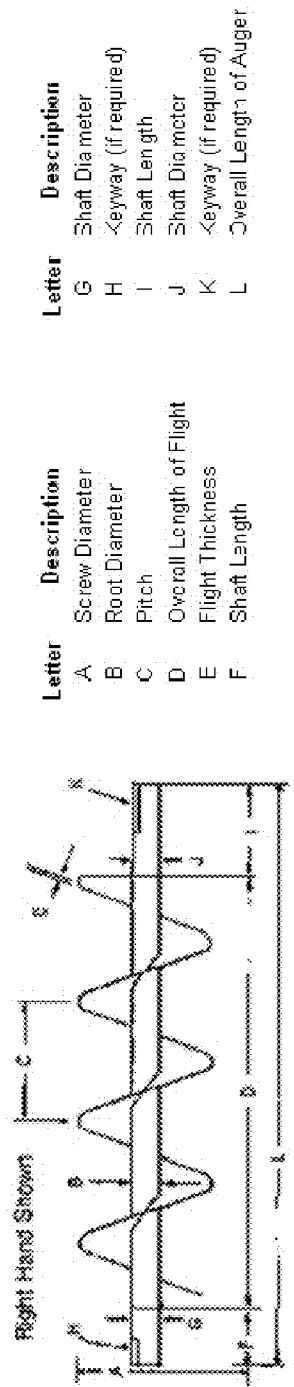

Right Hand Shown

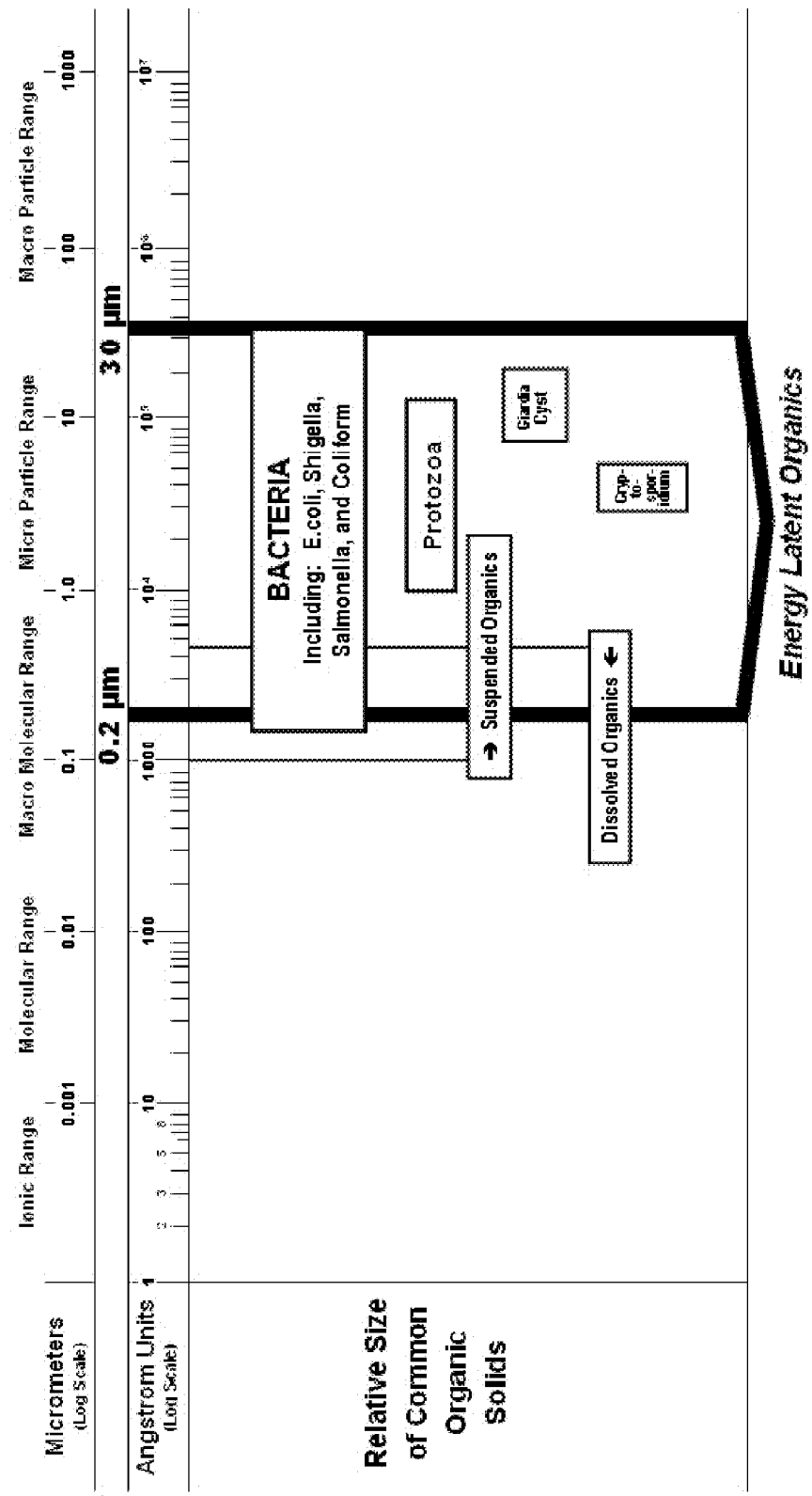

FOUR STAGE ANAEROBIC DIGESTER

CROSS REFERENCE TO RELATED APPLICATIONS

This Application claims the benefit of U.S. Provisional Application 61/286,773 filed on Dec. 15, 2009, the contents of which are expressly incorporated by reference in their entirety for all purposes.

BACKGROUND OF THE INVENTION

The present invention relates generally to production of biogas from wastewater treatment, and more specifically to multistage anaerobic digesters to improve production of biogas as a fuel source for combined heat and power (CHP) cogeneration.

Cities and municipalities are continually overburdened by energy, environmental, and water processing challenges. The US Department of Energy (DOE) has determined that 30% more electricity will be needed by 2025; thus, another challenge to become energy independent.

In the United States, our current power system is burdened with an increasing demand for more electricity. Moreover, the Electric Power Research Institute (EPRI) has projected in their 2003 Electricity Technology Roadmap that 7,000 GW of additional electric generation will be needed by the year 2050. The U.S. is also confronted with the ongoing conundrum of how to produce additional electricity without increasing the demand for more water, and without further contributing to greenhouse-gas emissions.

In April 2005, a Lawrence Berkeley National Laboratory Study (E.O. Lawrence Berkeley National Laboratory Study, April 2005, LBNL-57451, expressly incorporated by reference for all purposes) estimated the electricity potential from methane produced by the anaerobic digestion of wastewater biosolids from Industrial, Agriculture, and Municipal facilities. In Table 1, a segment of their Summary of Electricity Production and Emissions Reductions are shown; if the electricity were generated from fossil fueled power plants on the electricity grid. From the facilities in this segment, the Study calculated a total annual production potential of 8,900 GWH of electricity; more than the 2005 production of Hoover Dam, Glen Canyon Dam, and Shasta Dam, combined; with 3,233, 3,209, and 1,806 GWH respectively. Most importantly, this energy is readily available, without building new coal fired power plants or adding to the electricity grid infrastructure; saving untold billions of dollars.

TABLE 1

Summary of Clean Energy Technologies Potential
(NOTE: $CO_2$ @ million metric tons)

| Technology | Electricity Production (GWH/year) | Emissions Reduction (metric ton) | | | |
|---|---|---|---|---|---|
| | | $CO_2$ | $NO_x$ | $SO_x$ | Hg |
| Industrial Wastewater | 300 | 0.16 | 199 | 695 | 0.00 |
| Agriculture Wastewater | 1,400 | 0.82 | 993 | 3,478 | 0.02 |
| Municipal Wastewater | 7,200 | 4.20 | 5,091 | 17,835 | 0.09 |
| TOTAL: | 8,900 | 5.18 | 6,283 | 22,008 | 0.11 |

Over a 10-year period, the above Clean Energy Technologies Potential is equivalent to removing 57,100,000 ton of $CO_2$ from the environment and a reduction of 163,170,000 barrels of imported oil, thereby reducing foreign payments by $9,790,200,000-@ $60 per barrel.

The treatment and production of sewage sludge is the most energy intensive component in Wastewater Treatment (WWT), consuming up to 60% of the total energy requirements of a municipal WWT plant. In the United States, this equates to an annual consumption of 12.6 billion kilowatt hours of electricity, while simultaneously producing more than 10 million tons of sewage sludge. Conspicuously, the production of this sewage sludge has created a massive waste disposal, environmental, and sustainability problem.

Prior to the mid-1940's sewage sludge was neither a consideration nor an environmental problem because untreated wastewater was simply discharged directly into local waterways, carrying a heavy load of bacteria and other unwanted organisms along with it. After the mid-1940's, the WWT plants that were constructed had the ability to process, treat, and separate the sludge from raw sewage. Thus, began the era of the energy intensive production of sewage sludge and its inherent disposal, environmental, and sustainability issues.

Subsequently, rather than address the disposal problems associated with sewage sludge, many municipalities began constructing new WWT systems that employed the same old technology, rather than encourage the development of new techniques. This shortsightedness was primarily due to the availability of massive federal funding, promulgated by the 1972 Water Pollution Control Act, whose treatment infrastructure lessened the need to search for the most cost effective solution.

Recent advances have introduced newer treatment techniques: such as large-scale activated sludge systems, advanced anaerobic digestion processes that significantly enhance the breakdown of organic materials, and single-stage and multi-stage anaerobic digestion (AD) with biogas utilization for the production of combined heat and power (CHP). In spite of the incremental advances that have been made with these similar sludge treatment processes, the production of sewage sludge still remains energy intensive and the massive disposal, environmental, and sustainability problems still persists.

The CHP recovery potential at WWT plants can represent an important policy lever for sustainability. The Water Environment Research Foundation (WERF) has stated that sewage contains 10 times the energy needed to treat it. Dr. Mark Shannon, University of Illinois at Urbana-Champaign, addressing Chicago's WWT issues, has stated that harvesting methane from Chicago's sludge could yield a potential 5 mega-joules of energy from each cubic meter of wastewater treated (5,385 kilowatt hours per million gallons treated). This sludge potential has more than 12 times the energy produced with current AD processes. Accepting these authoritative energy potentials, and aware of the inherent limitations, it is unlikely that the current AD technologies will ever approach these projections without the achievement of a major breakthrough.

In California, there are 293 cities and towns with wastewater flow rates in the range of 0.1 to 5 MGD. The EPA has evaluated the current AD technologies and has established that flow rates of 5 MGD or less to be the lower economical limit for co-generation, also known as Combined Heat and Power. By transforming outdated, energy intensive wastewater treatment plants into energy producing Resource Recovery Plants, in these small cities and towns, the annualized excess electricity production could be greater than 78,000 megawatt hours. This excess electricity would be fed directly into the local grids. The overall net-energy advantage could exceed 646,000 megawatt hours of electricity. This is an unlimited, renewable energy source that equates to 80% of the U.S. 2009 net-electricity generation from Solar Thermal/PV, without adding to the electricity grid infrastructure. The net-energy advantage is also equivalent to removing more than 519,000 tons of carbon dioxide from the environment.

An energy producing Resource Recovery Plant should:
1. Reduce by more than 50% the cost to upgrade and the cost to build new WWT facilities.
2. Reduce the operational footprint by 80% (50'×50' per MGD), and recover unused land.
3. Operate 24/7/365 indoors and provide redundancy, with modular scalability for the future.
4. Avoid sewage sludge and related costs.
5. Reduce operation and maintenance costs by 25%.
6. Eliminate current electricity costs: 2,500 kWh/MG. (kilowatt-hours per million gallons processed)
7. Produce electricity @: 1,400 kWh/MG.
8. Consume electricity @: −750 kWh/MG.
9. Sell excess electricity to local grid: 650 kWh/MG.
10. Attain a net energy advantage: 3,150 kWh/MG.
   Example: Any City, U.S.A, (~1,000 population) processing 0.1 MGD, will realize a net energy advantage of 115,000 kWh annually.
   Any City, U.S.A, (~10,000 population) processing 1 MGD, will realize a net energy advantage of 1.15 million kWh annually.
   Any City, U.S.A, (~50,000 population) processing 5 MGD, will realize a net energy advantage of 5.75 million kWh annually.
11. Give 15,610 WWT facilities, with flow rates of 5 MGD or less, the option to become energy positive.
12. Qualify for EPA's ENERGY STAR label for Superior Energy Efficiency.
13. Qualify for State and Federal rebates and carbon and energy credits.

What is needed is a synergistic Resource Recovery Plant Concept designed to: 1) Filter wastewater to EPA standards; 2) Quantitatively recover the energy latent organics from the wastewater; 3) Transfer those organics to a 4-Stage Anaerobic Digester; 4) Produce and generate a maximum amount of methane and electricity—all occurring within minutes, instead of days; 5) Avoid sewage sludge; and 6) Reduce the operational footprint by 80%.

BRIEF SUMMARY OF THE INVENTION

Disclosed is a synergistic Resource Recovery Plant Concept designed to: 1) Filter wastewater to EPA standards; 2) Quantitatively recover the energy latent organics from the wastewater; 3) Transfer those organics to a 4-Stage Anaerobic Digester; 4) Produce and generate a maximum amount of methane and electricity—all occurring within minutes, instead of days; 5) Avoid sewage sludge; and 6) Reduce the operational footprint by 80%.

A multistage anaerobic digester for treatment of wastewater including complex organic polymers, includes a hydrolysis stage converting the complex organic polymers received at an inlet to solubilized monomers at an outlet; an acidogenesis stage, coupled to the outlet of the hydrolysis stage, converting the solubilized monomers into intermediate products at an outlet of the acidogenesis stage; an acetogenesis stage, coupled to the outlet of the acidogenesis stage, converting the intermediate products into simple molecules at an outlet of the acetogenesis stage; and a methanogenesis stage, coupled to the outlet of the acidogenesis stage, converting the simple molecules to an end product, the end product including a quantity of methane and a quantity of carbon dioxide.

A method for anaerobic digestion of wastewater including complex organic polymers includes a) passing the wastewater through successive stages of a multistage anaerobic digester using mechanical conveyors; and b) transforming, using enzymes immobilized to one or more elements of the mechanical conveyors in contact with the wastewater, the complex organic polymers into successively simpler compounds at each stage to produce an output gas at one of said stages of said digester, said output gas including predominately methane and carbon dioxide.

It is postulated that the inherent limitations with the current AD technologies are the inability to isolate the organics—from which the energy (methane to electricity) is generated—from the conventional production of sewage sludge. Embodiments of the anaerobic digester invention described in this patent, when combined with a Centrifugal Wastewater Filtration System (U.S. Pat. No. 7,686,965 issued Mar. 30, 2010, the contents of which are expressly incorporated by reference thereto in its entirety for all purposes) will overcome these limitations. The CWFS has the unique capability to filter wastewater, without creating sludge, and simultaneously isolate, concentrate and recover energy latent organics that are in the 0.2 to 30 micron range. Embodiments of this anaerobic digester invention when combined with a front-end process system, such as the CWFS described in U.S. Pat. No. 7,686,985, creates a Resource Recovery Plant.

The energy that can be recovered from wastewater is contained in the particulates that are in the 0.2 to 30 micron range as shown in FIG. 8, Filtration Spectrum, Size Range of Energy Latent Organics.

The filter industry has evolved to the point where sintered filters are now available that can withstand the radial forces generated in the Centrifugal Wastewater Filtration System (CWFS). Therein, the Energy Latent Organics can be quantitatively recovered from a wastewater influent stream and immediately transferred into the innovative 4-Stage Anaerobic Digester described in this patent.

The Anaerobic Digestion of organic matter in wastewater occurs in four sequential stages. See FIG. 1. Each stage of the AD process has its own optimum environment, i.e. concentration, temperature, and pH. For that reason, in order for each stage to attain maximum conversion in the shortest time frame (which can occur in minutes instead of days or weeks); it is essential that the stages are separated from one another. Even though recent advances have been made in AD technology, the current sewage sludge AD techniques will be unable to approach FDI's breakthrough 4-Stage AD energy recovery process, because of the inability to isolate, concentrate, and recover the Energy Latent Organics from sewage sludge.

Because the CWFS is designed to recover the Energy Latent Organics from the wastewater influent stream (approximately 1,700 pounds of BOD per million gallons) and immediately transfer those concentrated Energy Latent Organics into the 4-Stage AD, the Resource Recovery Plant will avoid sewage sludge.

The 4-Stage AD is projected to convert 80% of the Energy Latent Organic mass into methane and carbon dioxide. FDI further projects that the remaining environment friendly 340 pounds of Digestate will be designated Class A by the EPA; thus mitigating the ever-occurring waste disposal, environmental, and sustainability problems.

From the Shannon data, 5 mega-joules of energy potential per cubic meter of wastewater treated equates to 5,385 kWh/MG (based upon an average BOD concentration of 200 mg/L).

A recent Electric Power Research Institute (EPRI) study has shown that current AD processes can produce about 350 kWh/MG of wastewater treated, whereas a recent EPA-CHP Partnership estimates up to 525 kWh/MG can be produced. Although both figures are noteworthy, the energy production is still 10-15 times less than the WERF/Shannon projections.

The 4-Stage Anaerobic Digester should produce a minimum 1,400 kWh/MG of wastewater processed. This projection represents a considerable improvement over the cited EPRI/EPA energy production. Although this energy production is 3.9 times less than the WERF/Shannon energy projections, 1,400 kWh/MG is a good energy recovery starting point, for this state-of-the-art Concept.

Recognizing the fact that the 4-Stage Anaerobic Digester is in its early stages of development, and accepting the certainty of scientific improvements, it can be stated with confidence that further energy advances will be inevitable in the 4-Stage Anaerobic Digester; making the Resource Recovery Plant Concept the breakthrough technology capable of approaching the WERF/Shannon energy projections.

As a preface to the importance of this unique Resource Recovery Plant (Centrifugal Wastewater Filtration System and 4-Stage Anaerobic Digester), and the universal awareness of the inherent shortcomings throughout the wastewater treatment industry; the following quote from Bruce Logan, Professor of Environmental Engineering, Director, Penn State Hydrogen Energy Center, is provided.

"During the past 50 years, wastewater treatment has improved the quality of our navigable waters and the health of our environment. This achievement has not been accomplished without considerable capital investment by our nation, and we know that large expenditures will continue to be needed. It has been estimated that $2 trillion will be needed in the United States alone over the next 20 years for building, operating, and maintaining wastewater and drinking water facilities. Approximately $45 billion is needed for wastewater, in addition to the current annual expenditure of $25 billion. Where will we find such large reserves of funds for capital improvements and, even if we do, how will we justify the energy costs needed to run our wastewater treatment plants? Effective and efficient wastewater treatment is needed not just in the United States, but everywhere in a world as 2 billion people lack access to adequate sanitation. We are engaged in a new era of globalization, in which disease from one remote part of the world is only a plane ride away from anywhere else in the world. Wastewater treatment is not just a responsibility within the United States, but around the world. How will less industrialized and affluent nations afford to spend relatively enormous amounts of money on wastewater treatment?

"The technology of choice for domestic wastewater treatment in the United States is activated sludge, an energy-intensive aerobic process developed more than a century ago. How can we make so many advances in transportation, fuels, electronics, and other fields, and yet rely on the same basic process developed so long ago? It is clearly time to reexamine the energy costs of aerobic wastewater treatment systems and develop more innovative and less energy-consuming approaches. This need for innovation is recognized by our top wastewater scientists and engineers. A recent workshop sponsored by the Water Environment Research Foundation, Alexandria, Va., recommended that new wastewater treatment processes be developed that could produce products with a market value. Until recently, however, it was not clear what types of processes or products might fit this need."

The advantages of combining the CWFS with this 4-stage Anaerobic Digester are numerous. The combination will transform outdated, energy intensive Wastewater Treatment Plants into energy producing Resource Recovery Plants—with a carbon-negative footprint—attaining an approximate net-energy advantage of 3,150 kilowatt hours of electricity per million gallons of wastewater processed.

This transformation should prove to be so fundamental that the 15,610 municipal WWT facilities whose flow rates are 5 million gallons a day or less—EPA's established lower economical limit for CHP—will soon have the option to mitigate their wastewater, energy, and sustainability problems; by upgrading to energy producing Resource Recovery Plants. Assuming a 1 MGD average for the 15,610 facilities, the annualized net-energy advantage will equate to 1.80 billion kWh. Most importantly, this recurrent source of energy from wastewater is readily available, without building new coal fired power plants or adding to the electricity grid infrastructure; saving untold billions of dollars.

The Centrifugal Wastewater Filtration System and Anaerobic Digester technology represents a breakthrough Resource Recovery Plant Concept that can provide numerous advantages over current energy intensive WWT systems. The FDI technology will filter the wastewater and produce effluent to EPA standards; while simultaneously producing methane from its 4-Stage Anaerobic Digester to achieve net electrical energy—with a carbon-negative footprint.

Other advantages of the present invention will be seen by a review of the present disclosure.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 illustrates a diagram of the AD#1, AD#2, AD#3 and AD#4 housing configurations in series;

FIG. 7 provides a figure of anaerobic digester auger design parameters;

FIG. 8 illustrates the filtration spectrum showing the 0.2 to 30 micron range wherein the energy latent organics exists;

DETAILED DESCRIPTION OF THE INVENTION

Embodiments of the present invention provide a system, method, and computer program product for a synergistic Resource Recovery Plant Concept designed to: 1) Filter wastewater to EPA standards; 2) Quantitatively recover the energy latent organics from the wastewater; 3) Transfer those organics to a 4-Stage Anaerobic Digester; 4) Produce and generate a maximum amount of methane and electricity—all occurring within minutes, instead of days; 5) Avoid sewage sludge; and 6) Reduce the operational footprint by 80%. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Implementations of the present invention advantageously processes a substrate relatively free of unwanted constituents (of the type normally found in wastewater sludge) which improves an efficiency of conversion of the substrate to biogas. A centrifugal wastewater filtration system, such as that of the incorporated patent referenced herein, is a preferred modality for obtaining such a substrate. Other modalities may also provide an appropriate substrate for further processing and biogas generation by embodiments of the present invention.

Substrate (Energy Latent Organics within a 0.2-micron to 30-micron range) for the 4-Stage Anaerobic Digester (AD) can be obtained from a variety of wastewater sources, such as those in Municipal, Agriculture, and Industrial facilities. The wastewater will be processed in a Centrifugal Wastewater Filtration System (CWFS) that will have the ability to pre-adjust the concentration of the biologic oxygen demand (BOD) and/or chemical oxygen demand (COD) in order to optimize the production of biogas (~65% methane and ~35% carbon dioxide) as a fuel source for co-generation, also known as Combined Heat and Power (CHP). The substrate entering and leaving each Stage of the AD will be controllably maintained at a concentration and flow-rate that will collectively optimize the production of biogas for CHP.

Figure 1:
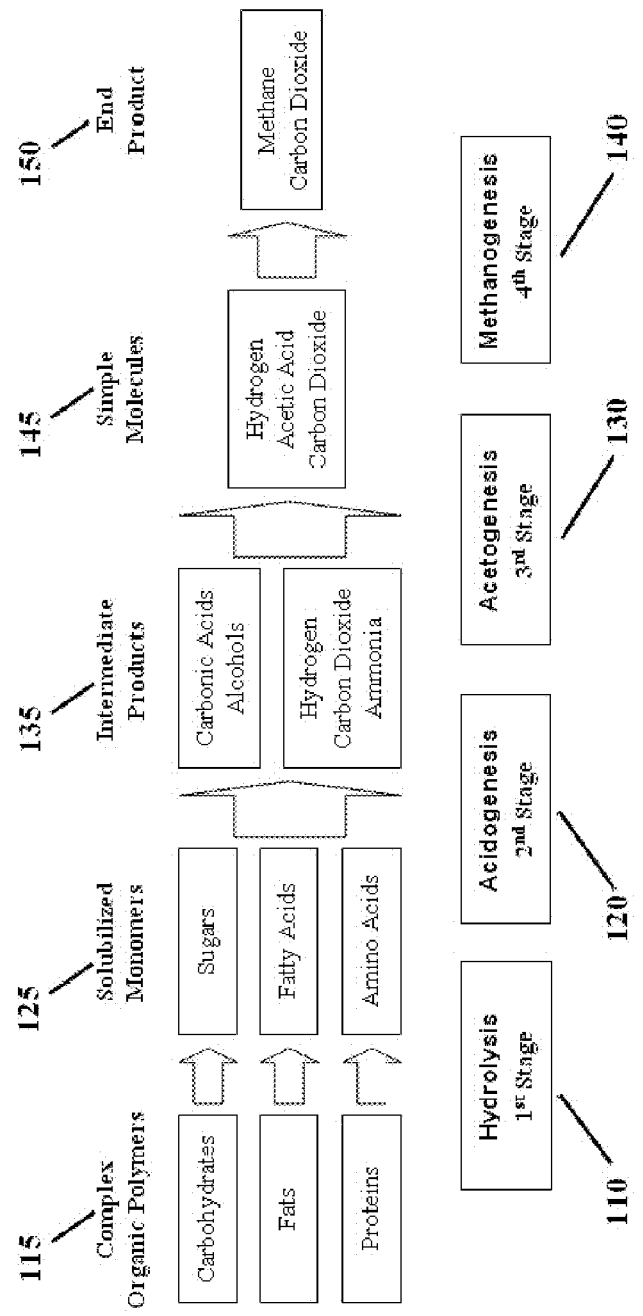
FIG. 1 illustrates a diagram of typical four stage enzymatic anaerobic digester pathway, from wastewater influent biological oxygen demand (BOD) or chemical oxygen demand (COD) to methane.
Figure 2:
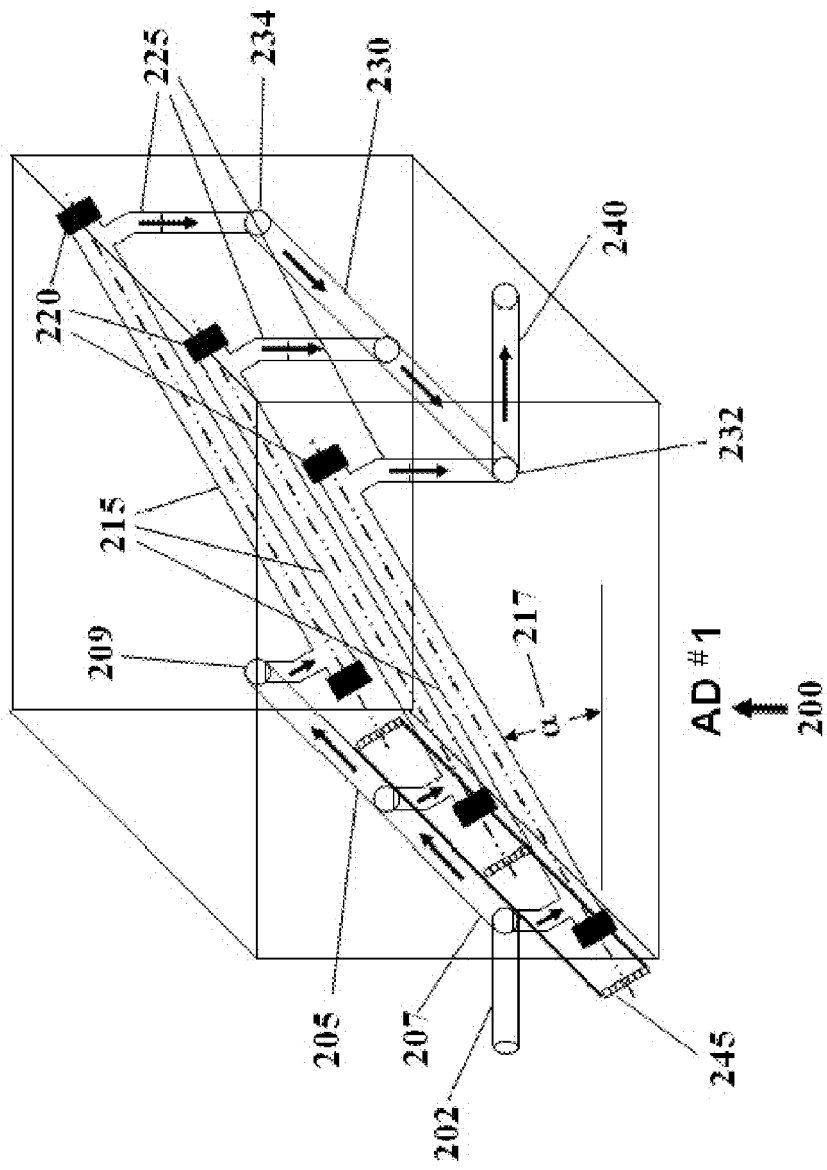
FIG. 2 illustrates a diagram of a the AD#1 housing configuration for the Hydrolytic first stage.
Figure 3:
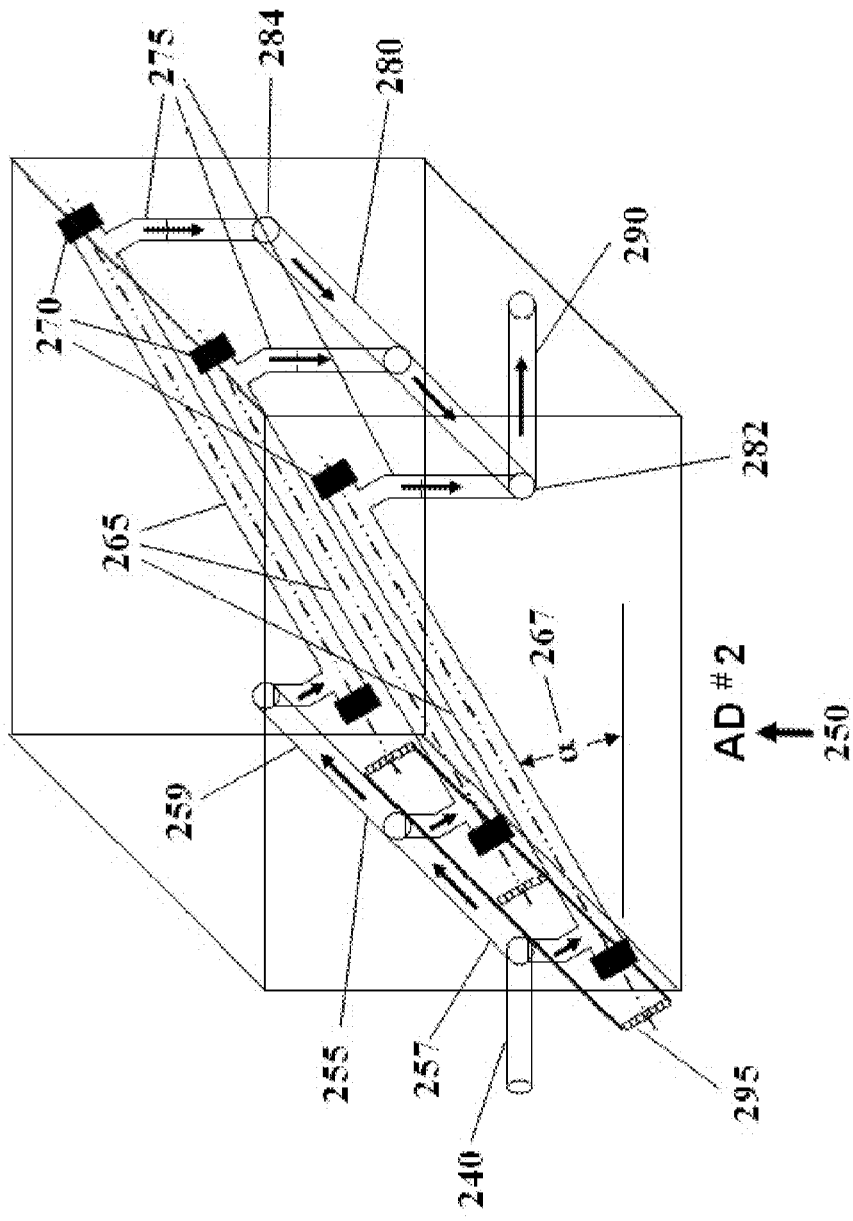
FIG. 3 illustrates a diagram of a the AD#2 housing configuration for the Acidogenic second stage.
Figure 4:
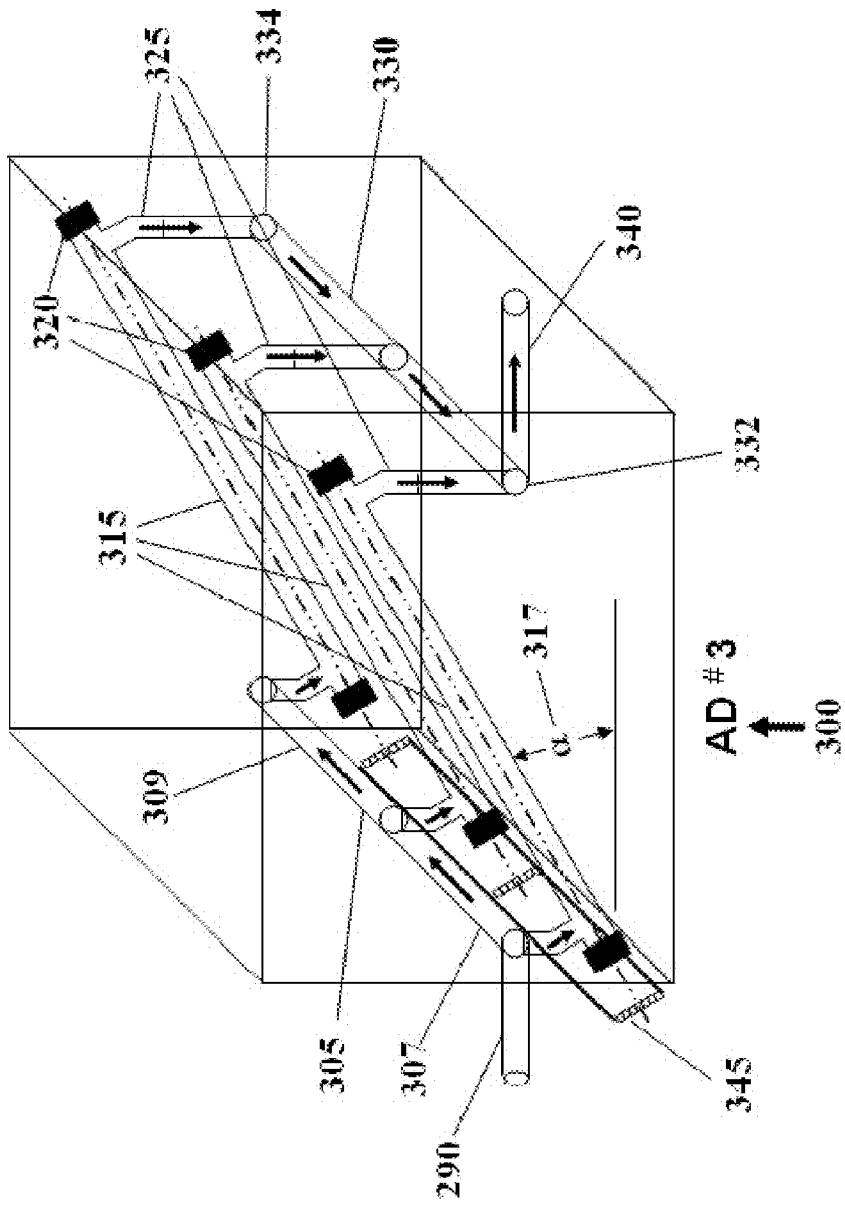
FIG. 4 illustrates a diagram of a the AD#3 housing configuration for the Acetogenic third stage.
Figure 5:
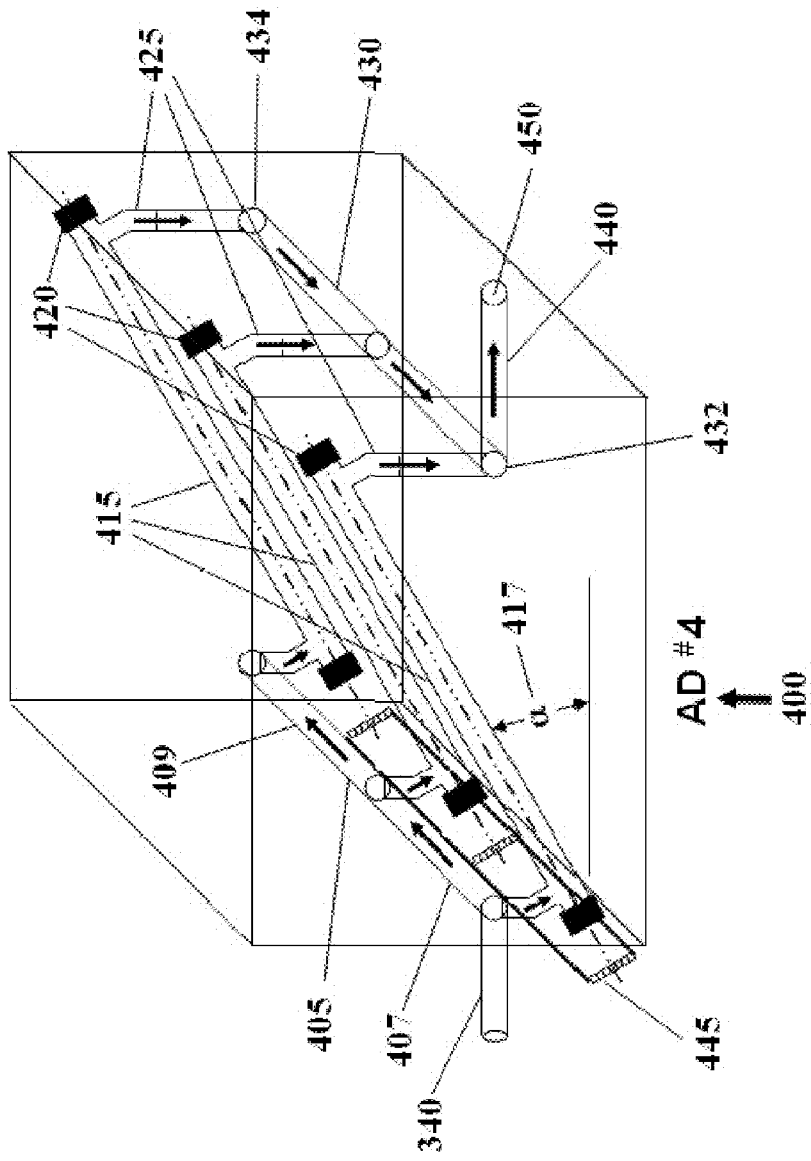
FIG. 5 illustrates a diagram of a the AD#4 housing configuration for the Methanogenic fourth stage.

FIG. 1 is a diagram of a four stage enzymatic anaerobic digester pathway having wastewater influent BOD and/or COD to methane effluent. The 1st Stage 110 of the AD receives the substrate directly from the CWFS. Therein, within a controlled environment (temperature, pH, etc.) the immobilized hydrolytic enzymes will transform the complex organic polymers in the substrate 115 into solubilized monomers 125 for immediate processing in the 2nd Stage 120.

The 2nd Stage 120 of the AD receives the solubilized monomers 125 directly from the 1st Stage 110. Therein, within a controlled environment (temperature, pH, etc.) the immobilized acidogenic enzymes will transform the solubilized monomers 125 into intermediate products 135 for immediate processing in the 3rd Stage 130.

The 3rd Stage 130 of the AD receives the intermediate products 135 directly from the 2nd Stage 120. Therein, within a controlled environment (temperature, pH, etc.) the immobilized acetogenic enzymes will transform the intermediate products 135 into simple molecules 145 for immediate processing in the 4th Stage 140.

The 4th Stage 140 of the AD receives the simple molecules 145 directly from the 3rd Stage 130. Therein, within a controlled environment (temperature, pH, etc.) the immobilized methanogenic enzymes will transform the simple molecules 145 into the End Product methane and carbon dioxide (biogas) 150. The methane 150 will then become a fuel source for co-generation, culminating in the production of combined heat and power.

At the end of the 4th Stage 140, it is anticipated that more than 90% of the Energy Latent Organics (substrate) will have been transformed into biogas 420 (~65% methane and ~35% carbon dioxide).

The final product, digestate 450, will be free of pathogens, and therefore be EPA rated as Class A, for disposal purposes. FIG. 2 through FIG. 5 are block schematic diagrams of housing configurations for each of stages 1 through 4, respectively. FIG. 6 is a block schematic diagram representing a series coupling of stages 1-4. The 1st Stage AD Housing 200 receives the complex organic polymers 115 (substrate) directly from the CWFS through the substrate entry piping 202. The complex organic polymers 115 enter the tapered auger feed piping 205, which feeds directly into a series of auger housings 215. The tapered auger feed piping 205 is tapered, beginning at the large end 207 to a smaller end 209, for the purpose of maintaining a constant pressure and flow of the complex organic polymers 115 into the auger housings 215. From the tapered auger feed piping 205 the auger housings 215 are set at an upward angle 217 to assure that the auger housings 215 are always filled with complex organic polymers 115 and also allow for the escape of any gas through the gas outlet valve 220 that may form within the auger housings 215 during the hydrolysis process. The gas outlet valve 220 will allow for the collection of that gas. Upon the completion of hydrolysis the solubilized monomers 125 will flow from the auger drain pipes 225 just below the top of the auger housings 215 and fall directly into the tapered auger outlet/feed piping 230 that is tapered, beginning at the large end 232 to a smaller end 234, and then flow from the housing connecting pipe 240 directly into the 2nd Stage AD Housing 250.

The 2nd Stage AD Housing 250 receives the solubilized monomers 125 directly from the housing connecting pipe 240 in the 1st Stage AD Housing 200. The solubilized monomers 125 enter the tapered auger feed piping 255, which feeds directly into a series of auger housings 265. The tapered auger feed piping 255 is tapered, beginning at the large end 257 to a smaller end 259, for the purpose of maintaining a constant pressure and flow of the solubilized monomers 125 into the auger housings 265. From the tapered auger feed piping 255 the auger housings 265 are set at an upward angle 217 to assure that the auger housings 265 are always filled with solubilized monomers 125 and also allow for the escape of any gas through the gas outlet valve 270 that may form within the auger housings 265 during the acidogenic process. The gas outlet valve 270 will allow for the collection of that gas. Upon the completion of acidogenesis the intermediate products 135 will flow from the auger drain pipes 275 just below the top of the auger housings 265 and fall directly into the tapered auger outlet/feed piping 280 that is tapered, beginning at the large end 282 to a smaller end 284, and then flow from the housing connecting pipe 290 directly into the 3rd Stage AD Housing 300.

The 3rd Stage AD Housing 300 receives the intermediate products 135 directly from the housing connecting pipe 290 in the 2nd Stage AD Housing 250. The intermediate products 135 enter the tapered auger feed piping 305, which feeds directly into a series of auger housings 315. The tapered auger feed piping 305 is tapered, beginning at the large end 307 to a smaller end 309, for the purpose of maintaining a constant pressure and flow of the intermediate products 135 into the auger housings 315. From the tapered auger feed piping 305 the auger housings 315 are set at an upward angle 317 to assure that the auger housings 315 are always filled with intermediate products 135 and also allow for the escape of any gas through the gas outlet valve 320 that may form within the auger housings 315 during the acetogenic process. The gas outlet valve 320 will allow for the collection of that gas. Upon the completion of acetogenesis the simple molecules 145 will flow from the auger drain pipes 325 just below the top of the auger housings 315 and fall directly into the tapered auger outlet/feed piping 330 that is tapered, beginning at the large end 332 to a smaller end 334, and then flow from the housing connecting pipe 340 directly into the 4th Stage AD Housing 400.

The 4th Stage AD Housing 400 receives the simple molecules 145 directly from the housing connecting pipe 340 in the 3rd Stage AD Housing 300. The simple molecules 145 enter the tapered auger feed piping 405, which feeds directly into a series of auger housings 415. The tapered auger feed piping 405 is tapered, beginning at the large end 407 to a smaller end 409, for the purpose of maintaining a constant pressure and flow of the simple molecules 145 into the auger housings 415. From the tapered auger feed piping 405 the auger housings 415 are set at an upward angle 417 to assure that the auger housings 415 are always filled with simple molecules 145 during the methanogenic process. Upon the completion of methanogenesis the End Product methane and carbon dioxide (biogas) 150 will flow upward out of the biogas collection valves 425 to then be available as a fuel source for co-generation, culminating in the production of combined heat and power. From the digestate exit pipe 440 the digestate 450 is recovered and can then be available for use as a fertilizer, or other such purposes.

Features of the preferred embodiments of the present invention include: the AD housings are in series, designated as Stage #1, #2, #3, and #4; the AD housings are in an anaerobic environment; each of the AD housing stages #1, #2, #3, and #4, are environmentally controlled for the maximum conversion of the substrate, within that housing; the auger housings are in parallel; the augers housings are at an upward angle from substrate inflow to the substrate outflow; the upward angle of the auger housings (to be determined for maximum conversion in each Stage) assures that the auger housings will always be filled with substrate and will also allow for any gases, including the final product methane and carbon dioxide, to move out of the auger housings for maximum recovery; the number of augers per housing may vary, according to the substrate volume to be processed; and the flow of the substrate through the AD housings will be adjustable to achieve maximum conversion.

FIG. 7 is a view of an anaerobic digester auger design and key elements thereof. The augers will move the energy latent organics (substrate) through each of the auger housings, with the AD Housings, at the same controllable flow rate.

Features of preferred implementation of the augers include: the rate of volume flowing through each housing will be identical so that one housing is not ahead or behind in volume flow; synchronous rotation within each housing is critical to achieve uniform volume flow and conversion; the augers within each housing will be identical, connected, and rotate at the same controllable rpm; the rpm of the augers, and therefore through the auger housings, 215, 265, 315, and 415 are adjustable to match the substrate influent flow volume and to achieve the optimum substrate transformation; within the AD housings there will be a Chain-sprocket auger drive 205, 245, 305, and 405 for AD housings #1, #2, #3, and #4, respectively; each auger will have a sprocket at its lower end connected to a chain that will rotate all augers, within that AD Housing, at the same rpm being chain driven by a variable speed motor; the augers will be constructed of a material that will be inert and capable of attachment, through immobilization, of the required enzymes; computational fluid dynamics modeling will determine the optimum pitch of the augers; and the surface area of the auger blades (screw diameter, pitch, and overall length of flight), upon which the enzymes are immobilized, will be optimized in order to achieve the maximum enzymatic action and substrate transformation in order to achieve complete conversion, which will result in the maximum methane recovery.

Enzymes (hydrolytic, acidogenic, acetogenic, and methanogenic) specific to each of the four Stages 200, 250, 300, 400; will be immobilized on the auger blades for that Stage. The immobilized enzymes in each stage 215, 265, 315, 415 will act as catalysts that will optimize the transformation of substrate for the next stage. The diameter, pitch, number of blades, blade surface area, and quantity of immobilized enzymes will be scalable for each of the four stages 200, 250, 300, 400, to achieve the optimum substrate transformation. The substrate retention time within each auger housing 215, 265, 315, 415, will be manually or automatically controllable, based upon the substrate concentration and substrate influent volume; in order to achieve the optimum substrate transformation. However, the volume flow through each AD housing 215, 265, 315, 415 must be identical. Enzymes will be covalently bound to the augers at a concentration that will accommodate a broad range of BOD concentrations in the substrate, and thus assure complete enzymatic conversion of the substrate in each of the four stages 200, 250, 300, 400. Each of the four stages 200, 250, 300, 400 will be environmentally controlled for concentration, temperature, and pH, in order to achieve the optimum transformation for the production of the maximum End Product methane and carbon dioxide (biogas) 150.

The 4-Stage AD is scalable over a broad range of volumes, by, for instance, varying the number of auger housings, 215, 265, 315, 415 within each housing Stage 200, 250, 300, 400; varying the pitch and/or number of blades on each auger; varying the rpm of the augers within the auger housings, 215, 265, 315, 415. The flow of the substrate influent(s), 202, 240, 340, into each housing Stage 200, 250, 300, 400, coupled with the volume flow by the augers, may/will create a siphon effect that will reduce the energy required to move the substrate through the system. The first three housing Stages, 215, 265, 315, may not require gas exit ports because gas may not be produced, during substrate transformation within that stage. However, gas exit ports will be an option.

It is anticipated that when the substrate only contains Energy Latent Organics within the range of 0.2-30 microns, then the End Product methane and carbon dioxide (biogas) 150 will not require further purification (cleaning) to achieve maximum combustion with either an internal combustion engine or a turbine, to power a generator for production of electricity.

Figure 9:
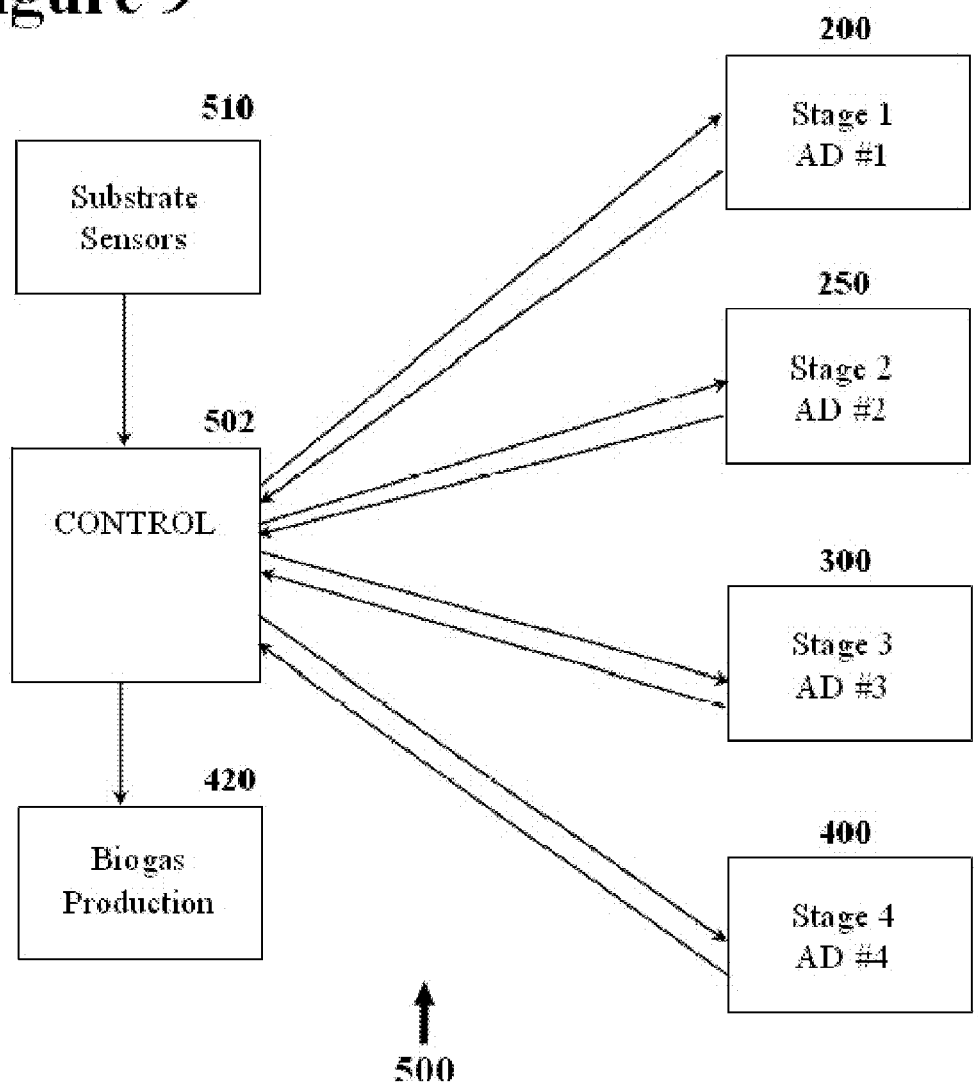
FIG. 9 illustrates a block diagram for either a manual or algorithmic control of the system.

FIG. 9 illustrates a block diagram for manual or algorithmic control of the system. Algorithmic control 500 can be automatic or semi-automatic as desired. Auger rotation speed, temperature and pH balance can be adjusted and controlled 502 manually or algorithmically to balance a broad range of substrate concentration volumes and/or biogas production volumes. Auger rotation speed, temperature and pH balance will be monitored and controlled in 200, 250, 300 and 400. Additional control flow-through and volume sensor units may be added as needed.

Figure 10:
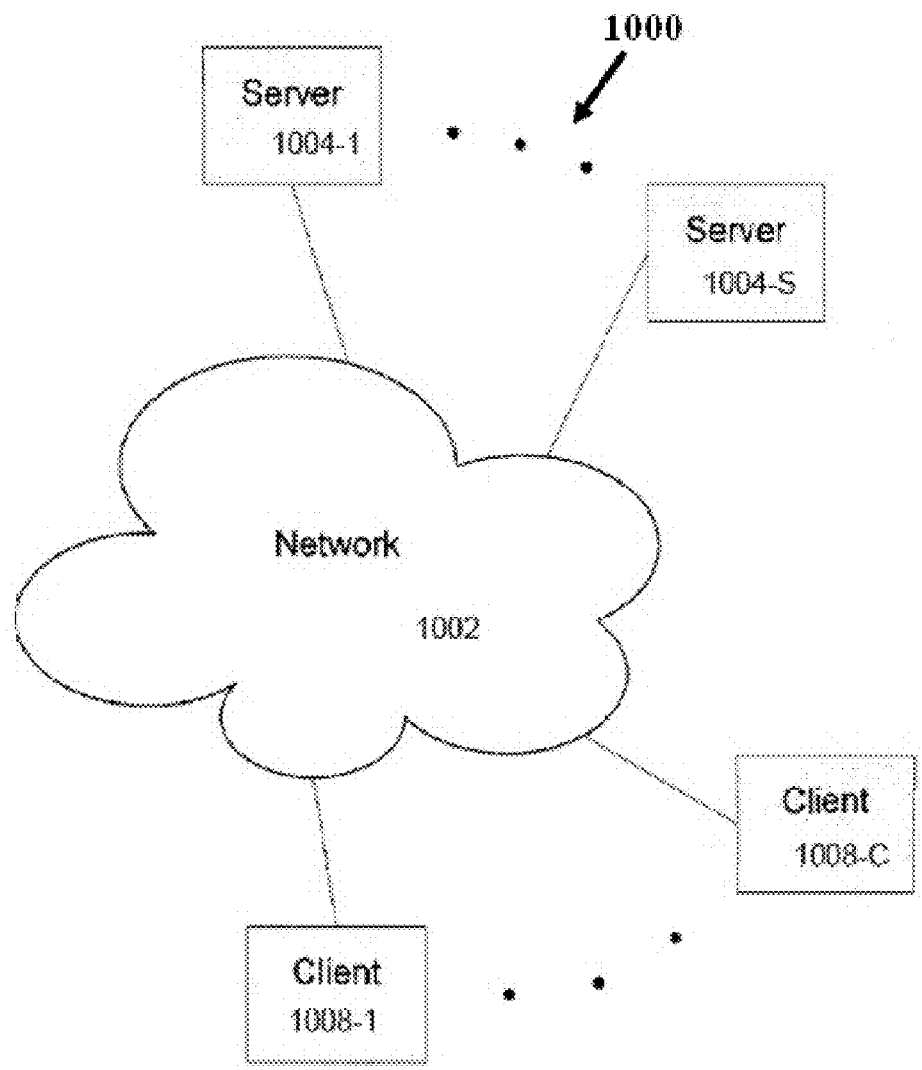
FIG. 10 illustrates a network environment for controlling the system.
Figure 11A:
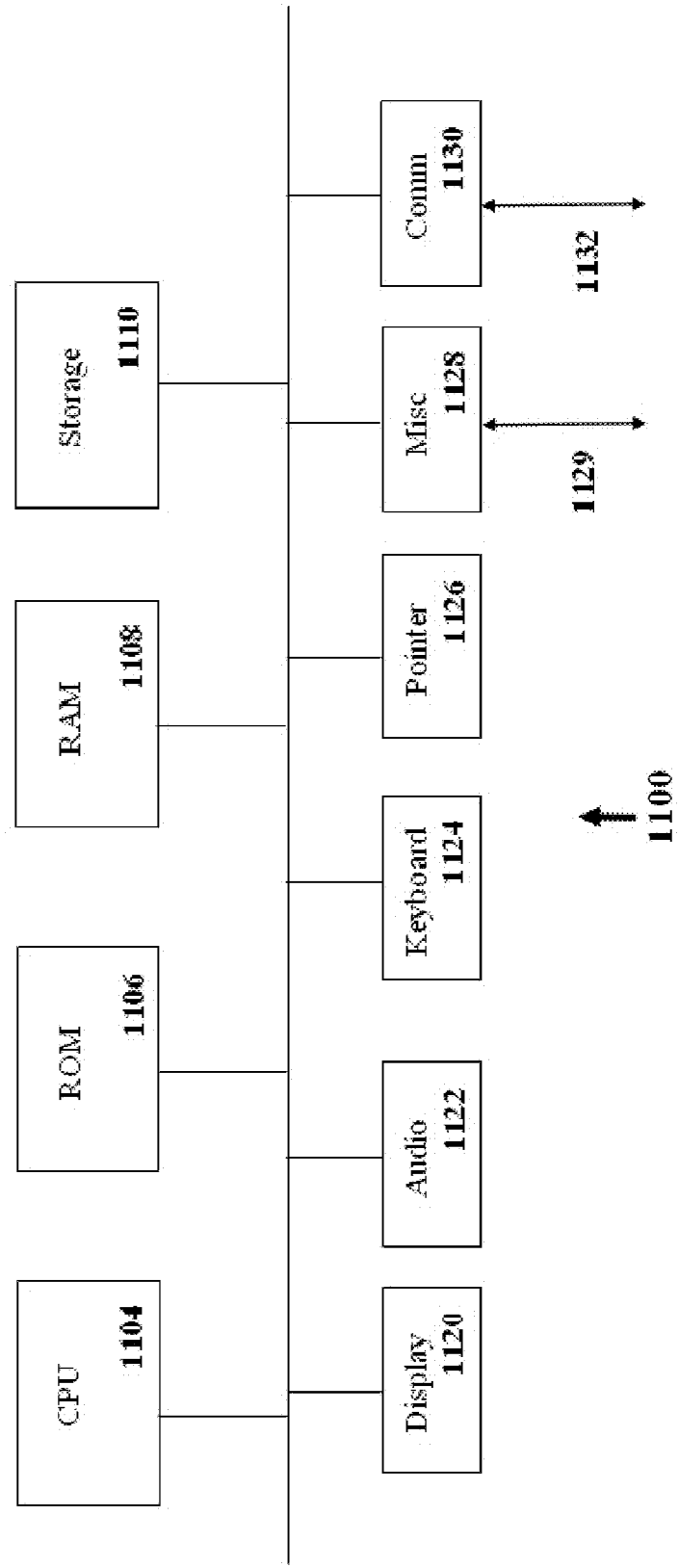
FIGS. 11A-B illustrate a computer system in which embodiments of the invention are controlled.
Figure 11B:
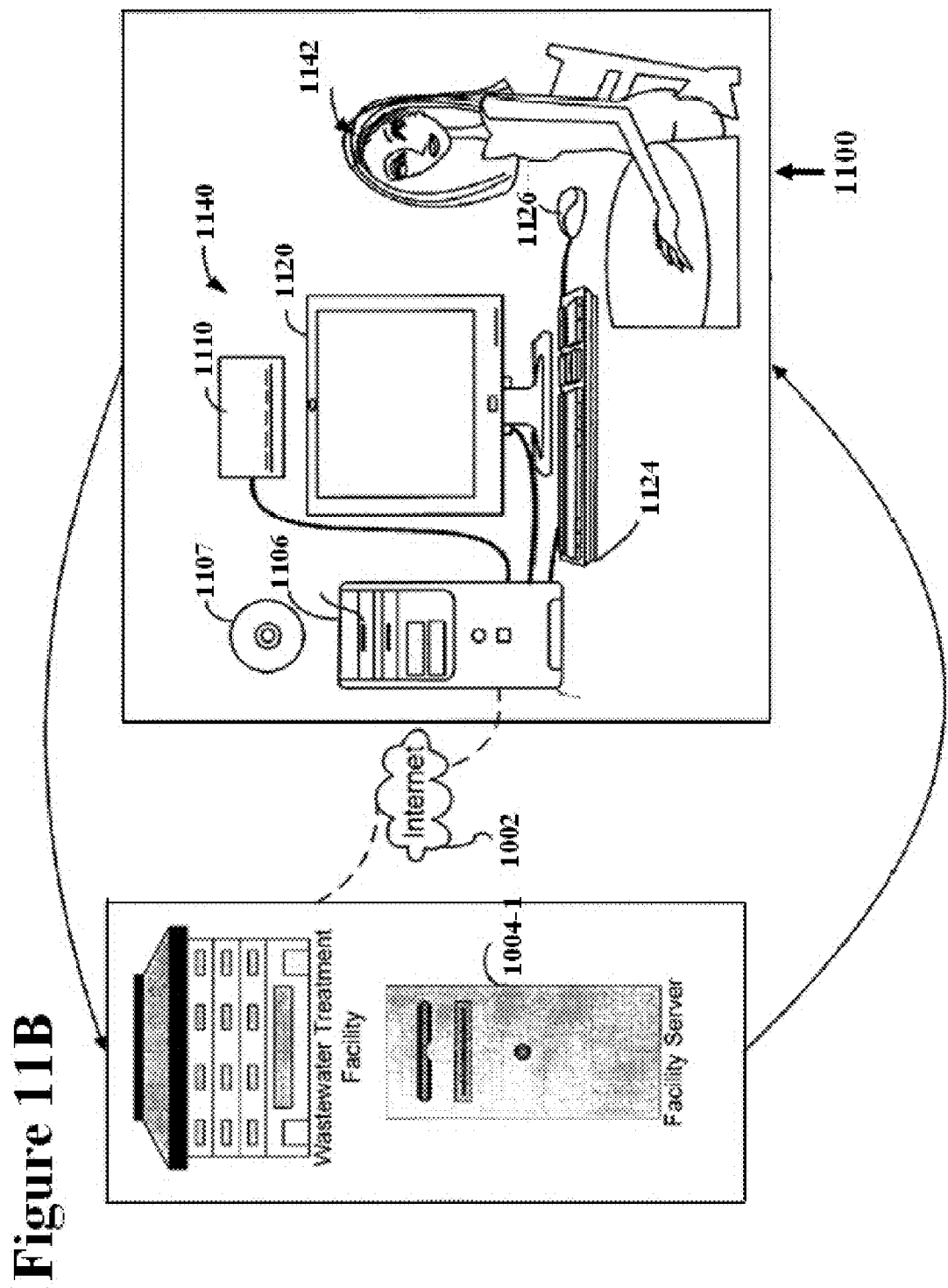

FIG. 10 illustrates a network environment 1000 for controlling the system in which the techniques described may be controlled and/or monitored. The network environment 1000 has a network 1002, such as an Internet connection, that connects one or more servers 1004-1 through 1004-S, and one or more clients 1008-1 through 1008-C. FIGS. 11A-B illustrate a computer system 2000, which may be representative of any of the clients and/or servers shown in FIG. 10, as well as, devices, clients, and servers in other Figures.

Referring back to FIG. 10, FIG. 10 illustrates a network environment 1000 in which the techniques described may be controlled and/or monitored. The network environment 1000 has a network 1002 that connects servers 1004-1 through 1004-S, and clients 1008-1 through 1008-C. As shown, several computer systems in the form of servers 1004-1 through 1004-S and clients 1008-1 through 1008-C are connected to each other via a network 1002, which may be, for example, a corporate based network. Note that alternatively the network 1002 might be or include one or more of: the Internet, a Local Area Network (LAN), Wide Area Network (WAN), satellite link, fiber network, cable network, or a combination of these and/or others. The servers may represent, for example, disk storage systems alone or storage and computing resources. Likewise, the clients may have computing, storage, and viewing capabilities. The method and apparatus described herein may be applied to essentially any type of visual communicating means or device whether local or remote, such as a LAN, a WAN, a system bus, etc. Thus, the invention may find application at both the S servers 1004-1 through 1004-S, and C clients 1008-1 through 1008-C.

Referring back to FIGS. 11A-B, FIGS. 11A-B illustrates a computer system 1100, which may be representative of any of the clients and/or servers shown in FIG. 10. The computer system 1100 may be configured to operate automatically or semi-automatically after initiation. The system can include a works station 1140 operated by a user 1142 who is either located within the wastewater treatment facility, or remotely located to the facility and connected by a server, e.g. through the Internet. The block diagram is a high level conceptual representation and may be implemented in a variety of ways and by various architectures. Bus system 1102 interconnects a Central Processing Unit (CPU) 1104, Read Only Memory (ROM) 1106, Random Access Memory (RAM) 1108, storage 1110, display 1120 (for example, embodiments of the present invention), CD or DVD 1107 capability, audio, 1122, keyboard 1124, pointer or mouse 1126, miscellaneous input/output devices 1128, and communications 1130. The bus system 1102 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (Firewire), Universal Serial Bus (USB), etc. The CPU 1104 may be a single, multiple, or even a distributed computing resource. Storage 1110, may be Compact Disc (CD), Digital Versatile Disk (DVD), hard disks (HD), optical disks, tape, flash, memory sticks, video recorders, etc. Comm 1130 via 1132 might be, for example, controlling an embodiment of the present invention, such as, but not limited to rpm, orifice control, etc. Note that depending upon the actual implementation of a computer system, the computer system may include some, all, more, or a rearrangement of components in the block diagram. For example, a thin client might consist of a wireless hand held device that lacks, for example, a traditional keyboard. Thus, many variations on the system of FIGS. 11A-B are possible.

Some portions of the description of the operation of the systems disclosed may be presented in terms of algorithms and symbolic representations of operations on, for example, data bits within a computer memory. Typically, algorithmic descriptions and representations are the means used by those of ordinary skill in the data processing arts to most effectively convey the substance of their work to others of ordinary skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, can refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, hard disks, optical disks, compact disk-read only memories (CD-ROMs), and magnetic-optical disks, read-only memories (ROMs), random access memories (RAMs), electrically programmable read-only memories (EPROM)s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with computer system configurations other than those described, including hand-held devices, multiprocessor systems, microprocessor-based or programmable consumer electronics, digital signal processing (DSP) devices, set top boxes, network PCs, minicomputers, mainframe computers, and the like. The invention can also be practiced in distributed computing environments where tasks are performed by remote processing devices that are linked through a communications network.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, etc.), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, or mathematical expression. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

Figure 12:
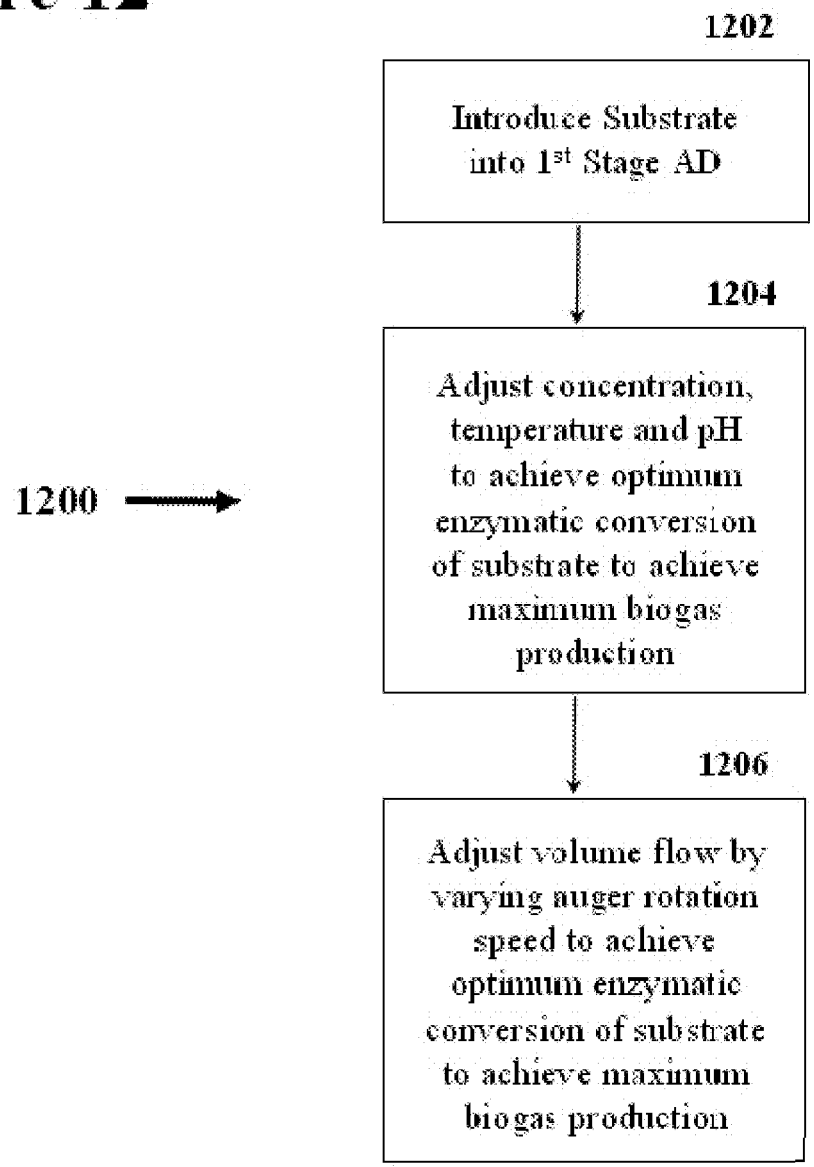
FIG. 12 is a block diagram showing the steps of a method for controlling the system.

FIG. 12 is a block diagram showing the steps of a method for controlling the system generally at 1200 in block diagram form. At 1202 an the substrate is introduced into 203 AD #1. At 1204 the temperature, concentration and pH is adjusted to achieve optimum enzymatic conversion of substrate to achieve maximum biogas production. At 1206 the auger rotation is adjusted to achieve optimum enzymatic conversion of substrate to achieve maximum biogas production. Thus a method and apparatus for anaerobic digestion have been described.

The system, method, and computer program product described in this application may, of course, be embodied in hardware; e.g., within or coupled to a Central Processing Unit ("CPU"), microprocessor, microcontroller, System on Chip, or any other programmable device. Additionally, the system, method, and computer program product, may be embodied in software (e.g., computer readable code, program code, instructions and/or data disposed in any form, such as source, object or machine language) disposed, for example, in a computer usable (e.g., readable) medium configured to store the software. Such software enables the function, fabrication, modeling, simulation, description and/or testing of the apparatus and processes described herein. For example, this can be accomplished through the use of general programming languages (e.g., C, C++), GDSII databases, hardware description languages (HDL) including Verilog HDL, VHDL, AHDL (Altera HDL) and so on, or other available programs, databases, nanoprocessing, and/or circuit (i.e., schematic) capture tools. Such software can be disposed in any known computer usable medium including semiconductor (Flash, or EEPROM, ROM), magnetic disk, optical disc (e.g., CD-ROM, DVD-ROM, etc.) and as a computer data signal embodied in a computer usable (e.g., readable) transmission medium (e.g., carrier wave or any other medium including digital, optical, or analog-based medium). As such, the software can be transmitted over communication networks including the Internet and intranets. A system, method, computer program product, and propagated signal embodied in software may be included in a semiconductor intellectual property core (e.g., embodied in HDL) and transformed to hardware in the production of integrated circuits. Additionally, a system, method, computer program product, and propagated signal as described herein may be embodied as a combination of hardware and software.

One of the preferred implementations of the present invention is as a routine in an operating system made up of programming steps or instructions resident in a memory of a computing system as well known, during computer operations. Until required by the computer system, the program instructions may be stored in another readable medium, e.g. in a disk drive, or in a removable memory, such as an optical disk for use in a CD ROM computer input or other portable memory system for use in transferring the programming steps into an embedded memory used in the charger. Further, the program instructions may be stored in the memory of another computer prior to use in the system of the present invention and transmitted over a LAN or a WAN, such as the Internet, when required by the user of the present invention. One skilled in the art should appreciate that the processes controlling the present invention are capable of being distributed in the form of computer readable media in a variety of forms.

Any suitable programming language can be used to implement the routines of the present invention including C, C++, Java, assembly language, etc. Different programming techniques can be employed such as procedural or object oriented. The routines can execute on a single processing device or multiple processors. Although the steps, operations or computations may be presented in a specific order, this order may be changed in different embodiments. In some embodiments, multiple steps shown as sequential in this specification can be performed at the same time. The sequence of operations described herein can be interrupted, suspended, or otherwise controlled by another process, such as an operating system, kernel, and the like. The routines can operate in an operating system environment or as stand-alone routines occupying all, or a substantial part, of the system processing.

In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

A "computer-readable medium" for purposes of embodiments of the present invention may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Embodiments of the invention may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of the present invention can be achieved by any means as is known in the art. Distributed, or networked systems, components and circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A multistage anaerobic digester for treatment of wastewater including complex organic polymers, comprising:
    a pre-treatment process by a Centrifugal Wastewater Filtration System (CWFS) having an output substrate of Energy Latent Organics that are within a 0.2-30 micron range;
    a hydrolysis stage converting the complex organic polymers, including said output substrate, received at an inlet to solubilized monomers at an outlet;
    an acidogenesis stage, coupled to said outlet of said hydrolysis stage, converting said solubilized monomers into intermediate products at an outlet of said acidogenesis stage;
    an acetogenesis stage, coupled to said outlet of said acidogenesis stage, converting said intermediate products into simple molecules at an outlet of said acetogenesis stage; and
    a methanogenesis stage, coupled to said outlet of said acidogenesis stage, converting said simple molecules to an end product, said end product including a quantity of methane and a quantity of carbon dioxide;
    wherein each said stage includes a self-contained compartment containing one or more angled augers, coated with immobilized enzymes, configured to transport the substrate from stage to stage.

2. The digester of claim 1 wherein a first-stage substrate carries said complex organic polymers through said hydrolysis stage, a second-stage substrate carries said solubilized monomers through said acidogenesis stage, a third-stage substrate carries said intermediate products through said acetogenesis stage, and a fourth-stage substrate carries said simple molecules through said methanogenesis stage.

3. The digester of claim 2 further comprising a controller coupled to each stage and wherein said controller maintains a concentration and a flow rate of each substrate within predetermined levels.

4. The digester of claim 3 wherein said predetermined levels produce said end product having a ratio of about 65% methane and about 35% carbon dioxide.

5. The digester of claim 2 wherein each stage includes a housing having one or more mechanical conveyors for traversing each substrate from an inlet to said outlet, each conveyor including immobilized enzymes appropriate for its stage which catalyze transformation of said influent material to said effluent material.

6. The digester of claim 5 wherein said mechanical conveyors each include one or more augers, each auger having a screw diameter and blade pitch, blade number, and blade surface area configured for enhancing substrate transformation.

7. The digester of claim 5 wherein each housing provides a controlled environment for its substrate, said controlled environment setting a temperature and a pH adapted for each substrate and transformation.

8. The digester of claim 5 wherein said mechanical conveyors of each said stage are arranged to provide a receiving piping tapered from an inlet having a first diameter to an outlet having a second diameter smaller than said first diameter with said tapering aiding in maintenance of a relatively constant pressure and flow rate of said substrate.

9. The digester of claim 8 wherein one or more of said mechanical conveyors are tilted upwards from said inlet to said outlet.

10. The digester of claim 9 wherein said one or more mechanical conveyors include a gas outlet valve for collection of any gas produced during that stage.

11. A method for anaerobic digestion of a wastewater substrate including complex organic polymers, the method comprising the steps of:
 a) pre-treating the wastewater substrate using a pre-treatment process by a Centrifugal Wastewater Filtration System (CWFS) having an output substrate of Energy Latent Organics that are within a 0.2-30 micron range;
 b) passing the wastewater substrate, including said output substrate, through successive stages of a multistage anaerobic digester using augers as mechanical conveyors; and
 c) transforming, using enzymes immobilized to one or more elements of the augers of the mechanical conveyors in contact with the wastewater, the complex organic polymers into successively simpler compounds at each stage to produce an output gas at one of said stages of said digester, said output gas including predominately methane and carbon dioxide.

12. The method of claim 11 wherein said multistage digester includes a pretreatment, a hydrolysis stage, an acidogenesis stage, an acetogenesis stage, and a methanogenesis stage and wherein a first-stage substrate carries said complex organic polymers through said hydrolysis stage, a second-stage substrate carries said solubilized monomers through said acidogenesis stage, a third-stage substrate carries said intermediate products through said acetogenesis stage, and a fourth-stage substrate carries said simple molecules through said methanogenesis stage.

13. The method of claim 12 further comprising a controller coupled to each stage and wherein said controller maintains a concentration and a flow rate of each substrate within predetermined levels.

14. The method of claim 13 wherein said predetermined levels produce said end product having a ratio of about 65% methane and about 35% carbon dioxide.

15. The method of claim 12 wherein each stage includes a housing having one or more mechanical conveyors for traversing each substrate from an inlet to said outlet, each conveyor including immobilized enzymes appropriate for its stage which catalyze transformation of said influent material to said effluent material.

16. The method of claim 15 wherein said mechanical conveyors each include one or more augers, each auger having a screw diameter and blade pitch, blade number, and blade surface area configured for enhancing substrate transformation.

17. The method of claim 15 wherein each housing provides a controlled environment for its substrate, said controlled environment setting a temperature and a pH adapted for each substrate and transformation.

18. The method of claim 15 wherein said mechanical conveyors of each said stage are arranged to provide a receiving piping tapered from an inlet having a first diameter to an outlet having a second diameter smaller than said first diameter with said tapering aiding in maintenance of a relatively constant pressure and flow rate of said substrate.

19. The method of claim 18 wherein one or more of said mechanical conveyors are tilted upwards from said inlet to said outlet.

20. The method of claim 19 wherein said one or more mechanical conveyors include a gas outlet valve for collection of any gas produced during that stage.

* * * * *